United States Patent
Grünenfelder et al.

(10) Patent No.: US 9,733,018 B2
(45) Date of Patent: Aug. 15, 2017

(54) DENTAL FURNACE

(71) Applicant: Ivoclar Vivadent AG, Schaan (LI)

(72) Inventors: Robert Grünenfelder, Eschen (LI); Philipp Kettner, Rankweil (AT); Harald Bürke, Frastanz (AT)

(73) Assignee: Ivoclar Vivadent AG, Schaan (LI)

( * ) Notice: Subject to any disclaimer, the term of this patent is extended or adjusted under 35 U.S.C. 154(b) by 128 days.

(21) Appl. No.: 14/378,860

(22) PCT Filed: Jan. 13, 2014

(86) PCT No.: PCT/EP2014/050516
§ 371 (c)(1),
(2) Date: Aug. 14, 2014

(87) PCT Pub. No.: WO2014/111350
PCT Pub. Date: Jul. 24, 2014

(65) Prior Publication Data
US 2015/0010876 A1    Jan. 8, 2015

(30) Foreign Application Priority Data
Jan. 15, 2013 (EP) .................................. 13151340

(51) Int. Cl.
*F27B 5/18* (2006.01)
*F27B 17/02* (2006.01)
(Continued)

(52) U.S. Cl.
CPC ............ *F27B 17/025* (2013.01); *A61C 13/20* (2013.01); *F27D 19/00* (2013.01); *F27D 21/00* (2013.01); *F27D 21/02* (2013.01)

(58) Field of Classification Search
CPC ...... A61C 13/0004; F27B 17/025; F27B 5/18; F27D 2019/0003
(Continued)

(56) References Cited

U.S. PATENT DOCUMENTS 6,303,059 B1   10/2001 Foser et al.
7,001,178 B2 *  2/2006 Grunenfelder ......... A61C 13/20
                                                     432/206
(Continued)

FOREIGN PATENT DOCUMENTS

DE         3146391 A1   5/1983
DE    102006032655 A1   1/2008
(Continued)

*Primary Examiner* — Gregory A Wilson
(74) *Attorney, Agent, or Firm* — Ann M. Knab; Thad McMurray

(57) ABSTRACT

The invention relates to a dental furnace, in particular a firing furnace or press furnace, for firing or pressing a dental restoration part which is receivable in the furnace, possibly after pre-heating in a pre-heating furnace, and which is placeable on a base, in particular centrally thereon, wherein the dental furnace comprises a firing chamber whose diameter is larger than, in particular at least twice as large as, the largest dental restoration part to be fired, and which comprises a control device and an operating unit at the or for the dental furnace (10), wherein by means of the operating unit (26) the size and/or the weight and/or the number of the dental restoration part(s) (18) to be fired or pressed is adjustable in units.

19 Claims, 1 Drawing Sheet

(51) Int. Cl.
*A61C 13/20* (2006.01)
*F27D 19/00* (2006.01)
*F27D 21/00* (2006.01)
*F27D 21/02* (2006.01)

(58) Field of Classification Search
USPC .................................. 432/205, 206; 219/390
See application file for complete search history.

(56) References Cited

U.S. PATENT DOCUMENTS

| | | | |
|---|---|---|---|
| 7,131,784 B2 | 11/2006 | Lee et al. | |
| 8,109,761 B1 * | 2/2012 | Neal | F27B 17/025 |
| | | | 219/390 |
| 8,232,506 B2 * | 7/2012 | Jussel | A61C 13/20 |
| | | | 219/390 |
| 9,033,703 B2 * | 5/2015 | Rohner | A61C 13/20 |
| | | | 219/539 |
| 2003/0113685 A1 * | 6/2003 | Plank | A61C 19/004 |
| | | | 433/29 |
| 2004/0182538 A1 | 9/2004 | Lambrecht | |
| 2008/0237211 A1 | 10/2008 | Jussel et al. | |
| 2010/0047731 A1 * | 2/2010 | Zubler | A61C 13/20 |
| | | | 432/45 |
| 2013/0029281 A1 * | 1/2013 | Jussel | A61C 13/20 |
| | | | 432/32 |
| 2014/0231408 A1 * | 8/2014 | Jussel | H05B 1/025 |
| | | | 219/425 |
| 2014/0339216 A1 * | 11/2014 | Jussel | F27D 21/02 |
| | | | 219/390 |

FOREIGN PATENT DOCUMENTS

| | | |
|---|---|---|
| EP | 1440750 A1 | 7/2004 |
| EP | 1978321 A1 | 10/2008 |
| EP | 2550929 A1 | 1/2013 |
| JP | 2002-062117 A | 2/2002 |
| RU | 2063727 C1 | 7/1996 |

* cited by examiner

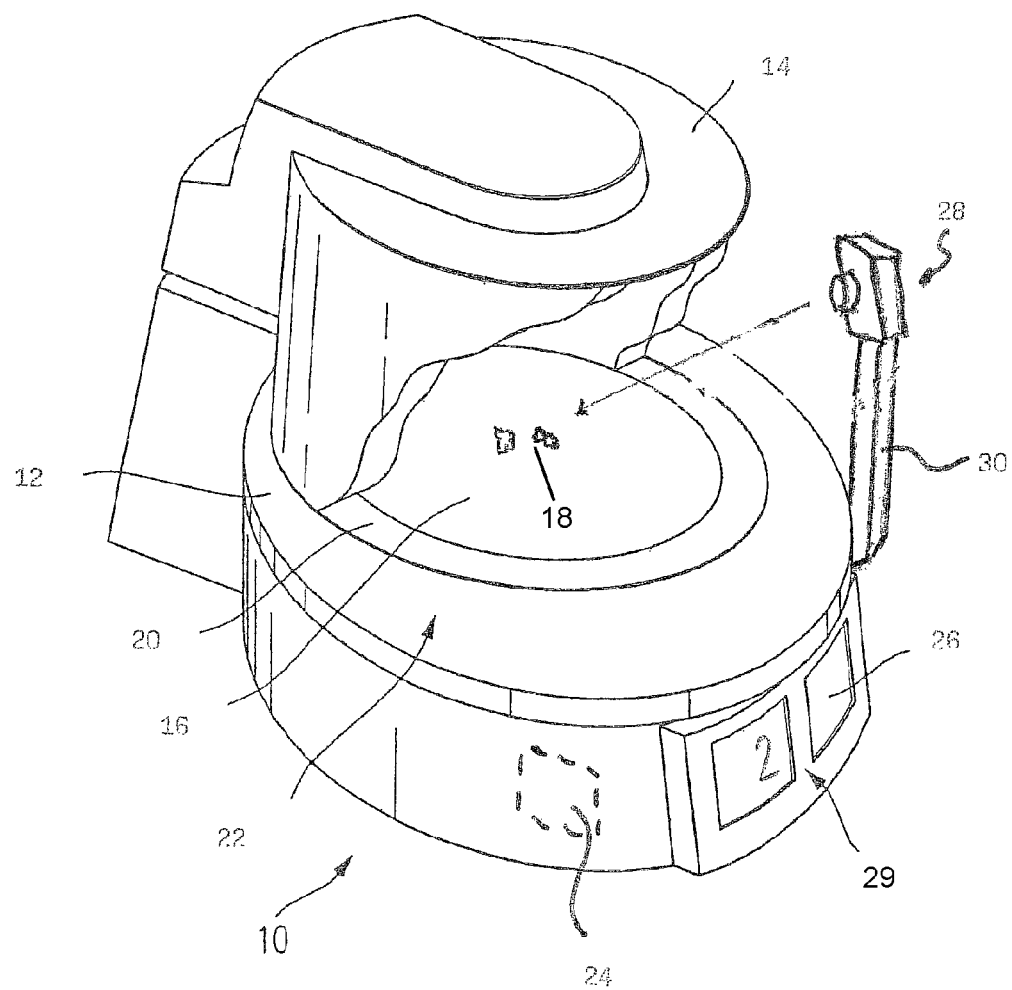

DENTAL FURNACE

CROSS-REFERENCE TO RELATED APPLICATIONS

This application is a National Stage application of International patent application PCT/EP2014/050516 filed on Jan. 13, 2014, which claims priority to European patent application No. 13 151 340.0 filed on Jan. 15, 2013, the disclosures of which are incorporated herein by reference in their entirety.

TECHNICAL FIELD

The invention relates to a dental furnace for firing or pressing a dental restoration part which is receivable in the furnace

BACKGROUND OF THE INVENTION

It has been known for long to provide dental furnaces with control devices which determine and control the exact course of the temperature curve of the dental restoration parts to be fired.

An example of an elaborate control of this type can be taken from DE 35 05 346 A1. In the solution known from this document the liquidus temperature of the molten material is detected by measuring the temperature course of the molten material as exactly as possible when heating power is supplied and by detecting the achieved increases in temperature per heating power supplied.

This solution suggested at that time already shows that it is not sufficient to simply predetermine an exact temperature/time profile for one specific dental furnace; in some cases, the current temperature that actually exists in the interior of the dental restoration part in practice deviates significantly from the furnace temperature.

In practice, the deviation value depends on numerous parameters. Among them are the size, the mass and the shape of the dental restoration parts, but also the material of which they are made, the melting temperature of the material, the specific thermal capacity, the arrangement of the dental restoration parts in the furnace—i.e. to that extent the distance to the heating which is most often arranged in a ring-shaped manner—, the heating rate, the amount of negative pressure in dental firing furnaces operated at negative pressure and the existing pressure exerted on the press blank in press furnaces.

Further parameters, such as ambient pressure and ambient temperature, can also play an important role in sections of the temperature profile already passed through.

In order to pass through the desired temperature as exactly as possible control panels for controlling the furnace have also been developed which serve to show the actual temperature and to symbolically represent the course of the temperature/time diagram. An example hereof can be taken from DE 31 46 391 A1.

When implementing such solutions, however, it turns out again and again that misfirings occurred in spite of careful attention to the specified manufacturer's instructions and settings of the plurality of parameters in a manner adjusted to the material, which means that dental restorations were produced which are of low quality.

Discolorations of ceramic parts can be at least partially compensated for by painting techniques in retrospect. If, however, the dental ceramic used is not fired at the desired temperature and the temperature course stipulated by the manufacturer, the specification of the ceramics is typically not complied with. For instance, lithium disilicate ceramics exhibit good biocompatibility which also involves no or only very limited signs of wear on the antagonist opposite from the dental restoration. If the exact temperature-pressing course is not adhered to, the favorable properties of this ceramic part may not be achieved or only to a reduced extent.

In the case of relatively old ceramic parts, or in the case of zirconium dioxide ceramics, depending on the case of application, brittle fractures resulting in corresponding recourse claims can occur.

In order to further minimize mistakes when firing dental restoration parts numerous suggestions and developments have been undertaken. For instance, attempts have been made to detect the temperature of the products to be fired more exactly, as is known, for instance, from DE 10 2007 035 609 A1. But still there is the need to eliminate or reduce risks in the firing process and the aforementioned problems.

SUMMARY OF THE INVENTION

Thus, the invention is based on the task of providing a dental furnace for firing or pressing a dental restoration part which is receivable in the furnace, which further minimizes or possibly even eliminates the risk of producing misfired parts or of producing dental restoration parts whose material properties are worsened compared to the specification.

According to the invention it is provided to use a sensor known per se as a detection device for a modified purpose. While the infrared sensors used up to now are intended to monitor the temperature of the surface of the dental restoration parts to be fired as exactly as possible, the invention deviates herefrom, and the infrared sensor is used to detect the size and/or the number of the dental restoration parts to be fired. By implication, the detection of the size also results in a detection of the weight, as, according to the invention, it is provided to convert the values detected into units of dental restoration parts.

This is explained on the basis of an example.

The inventive infrared sensor determines the size of the dental restoration part to be fired. This results in a size of, for instance, 2 mm by 3 mm. This size is assigned to the unit 1 and it is assumed that the dental restoration part is fired for only one single tooth, i.e. that it is, for instance, intended as a crown for one single tooth.

In the next firing process, the infrared sensor detects a size of 22 mm by 7 mm. Due to the length of 22 mm the inventive control device makes conversions and concludes that the dental restoration part must be a three-unit bridge, and thus it is detected that a correspondingly large and weighty dental restoration part is to be fired.

Now, the user adjusts the dental furnace to one unit in the first case, and to three units in the second case, corresponding to the recommended value offered by the control device on the display device.

In a third case, the detection device detects a size of 4 mm by 3 mm and a further size of 4 mm by 5 mm. The detection device supplies the control device with these values, which control device concludes upon standardization of the values that two crowns are to be fired, one slightly larger and one slightly smaller crown. At the same time, the detection device extracts the value of 2 as the number of dental restoration parts, and also supplies the control device with this value. In an advantageous embodiment, this value is now suggested to the user by the display device and the user adjusts the dental furnace according to the number of units.

Surprisingly, this inventive process is exceptionally secure and allows even unexperienced dental technicians to achieve good firing results.

In an advantageous embodiment the furnace itself additionally carries out a "vernier adjustment" in such a way that, if the detection device detects values at the upper end of the size associated with a unit, the temperature parameters are slightly increased, such as for a size of 4 mm by 5 mm for a unit, or slightly decreased if the size detected is at the lower end of the value associated with the unit, as is the case in the aforementioned first exemplary case at a size of 2 mm by 3 mm.

The invention is not limited to the use of an infrared sensor or a thermal imaging camera for the detection of sizes or weights. For instance, instead, a thermally protected strain gauge can be integrated in the furnace bottom which measures the load of the furnace bottom when dental restoration parts are placed on the furnace bottom. This measure also makes possible to determine the size or the weight of the dental restoration parts to be fired.

Equally, the invention can also be used with press furnaces in which the size and/or the weight of the muffle inserted will then be determined. Typically, multi-unit bridges are fired in larger muffles, i.e. muffles of, for instance, 300 g. Smaller dental restoration parts, by contrast, can be fired efficiently in smaller muffles of 200 g or even only 100 g. For instance, 4- to 9-unit bridges can be fired in large 300 g muffles, while 200 g muffles are typically sufficient for 3- to 5-unit bridges and 100 g muffles can be used for even smaller dental restoration parts.

In a press furnace, preferably, the numerical representation of units is not coupled to the number of units of a bridge or individual teeth but, for instance, to the size of the muffle such that a detected 100 g muffle would be represented with 1, a 200 g muffle with 2 and a 300 g muffle with 3. The size of the muffle can then in turn be detected by means of an infrared sensor or a weight sensor, in an inventively favorable manner.

The detection device is not limited to the sensors mentioned up to now either. To this extent, when the firing furnace or press furnace is opened, an optical camera can detect the design of the restoration parts or muffles to be fired, possibly even in a three-dimensional manner, for instance by means of two cameras which are arranged relative to one another at an angle and directed at the dental restoration part or the muffle, or by pivoting the camera by, for instance, 90 degrees. In this way, the size and thus implicitly the weight and explicitly the number of the dental restoration parts to be fired or pressed can be detected and can be quantified and/or standardized in units according to the invention and preferably offered to the user in this manner.

In a modified embodiment the furnace is adjusted practically automatically based on the determination of units, as described above, and the user is only informed about the determined size in a standardized way, for instance by means of a display device which displays the number of units.

Depending on the units determined the press program or the firing program is adjusted according to the invention, wherein user interaction is also favorably possible. However, possible user interaction preferably also comprises a logic check unit which prevents a firing program or a press program from being adjusted which does not match the adjusted unit value predetermined by the user.

In an advantageous embodiment it is provided that the dental furnace comprises a detection device connected to the control device and detecting the size and/or the number and/or the weight of the dental restoration part.

In an advantageous embodiment it is provided that the detection device supplies the control device with a value of the detected size and/or the number and/or the weight of the dental restoration part and that the control device quantifies this value and offers it to the user in a unit such as 1, 2, etc. by means of the operating unit.

In an advantageous embodiment it is provided that the dental furnace comprises a display device which can display the size and/or the weight of the dental restoration part in units.

In an advantageous embodiment it is provided that the operating unit comprises an operating panel which enables the setting of a press program or a firing program in units depending on the detected size or the detected weight of the dental restoration part.

In an advantageous embodiment it is provided that the operating unit enables the control via voice control and/or gesture control and/or via a remote control.

In an advantageous embodiment it is provided that a detection device detects the number and/or the size of the dental restoration part(s) to be fired or pressed and comprises an IR sensor or a camera.

In an advantageous embodiment it is provided that the detection device supplies the control device with the output signal of the IR sensor or the camera and that the control device comprises an image recognition device which recognizes individual regions of the image detected and assigns them to the dental restoration parts.

In an advantageous embodiment it is provided that the control device detects the number and/or size of the dental restoration parts by means of the image of the dental restoration parts detected by the IR sensor or the camera, based on a predetermined distance between IR sensor or camera and the dental restoration parts, and outputs the number and/or size based on the result of the recognition of the image of the dental restoration parts.

In an advantageous embodiment it is provided that the camera is designed as a thermal imaging camera and that in the image recognition of the image of the dental restoration parts detected by the detection device the outline of the hot areas corresponding to the hot dental restoration parts is distinguished from the cold surroundings and that based on this the number and/or the size of the dental restoration parts is determined.

In an advantageous embodiment it is provided that the detection device supplies the control device with a numerical value regarding the size and/or the weight of the dental restoration part and that the control device carries out a comparison with predetermined value ranges for quantification, similar to rounding, and supplies the display device with the rounded result for display in units.

In an advantageous embodiment it is provided that a detection device of the dental furnace is switched to active at the beginning of the press cycle or the firing cycle of the dental furnace and that when the dental restoration part approaches and/or is inserted into and/or placed into/on the dental furnace, the detection device automatically detects the number, the size and/or the weight of the dental restoration part.

In an advantageous embodiment it is provided that the dental restoration part is intended for being received in the dental furnace on a firing tray and that a detection device of the dental furnace detects the firing tray with regard to the weight, the size, i.e. height and/or diameter, and the density, i.e. the mass, thereof and that the control device introduces the parameters of the firing tray into the quantification.

In an advantageous embodiment it is provided that a firing aid of the dental furnace, such as a firing tray, comprises an encoding via which a detection device of the dental furnace recognizes it and carries out an automatic adjustment of the firing program or the press program.

In an advantageous embodiment it is provided that the control device carries out a correction factor for controlling the firing program or press program upon recognition of a firing tray or any other firing aid by the detection device and offers the correction as a correction factor or as a correction value to the user for selection, in particular on a display device.

BRIEF DESCRIPTION OF THE DRAWING

Further advantages, details and features may be taken from the following description of one exemplary embodiment in conjunction with the drawing.

The only FIGURE of the drawing shows:

FIG. 1 a schematically illustrated firing furnace comprising a display device in one embodiment of the invention.

DETAILED DESCRIPTION OF THE INVENTION

The dental furnace 10 shown in FIG. 1 comprises a furnace base 12 and a furnace top 14 which is mounted to the furnace base in a way known per se so as to effect a tilting and/or lifting motion similar to a firing hood. For this purpose, a joint (not further illustrated) is provided in a way known per se in the rear area of the dental furnace 10.

The firing hood is basically configured as a hollow cylinder wherein in a way known per se the furnace heating is provided at the cylinder wall. Thus, the firing chamber built in this way is also cylindrical. At the bottom it is limited by a furnace bottom 16 which is intended for receiving dental restoration parts 18. Here, in the exemplary embodiment illustrated two crowns are placed next to each other on the furnace bottom 16 as dental restoration parts.

The furnace top is supported by the furnace base 12 in a ring-shaped manner. It is sealed against it by a seal 20 such that negative pressure can be applied to the firing chamber.

The furnace bottom 16 is surrounded by a storage surface 22 which makes possible to place dental restoration parts which have already been fired thereat for cooling or to place dental restoration parts which are to be fired next thereat in preparation for the firing process.

According to the invention the dental furnace is provided with a control device 24 (not further illustrated) which allows for the control of the firing cycle depending on the adjusted firing program. Furthermore, an operating unit 26 is attached to the front of the furnace which comprises a touch screen in the exemplary embodiment illustrated.

The operating unit also comprises a display device wherein in the exemplary embodiment illustrated an additional and separate display device 29 is implemented which can, however, also be integrated in the operating unit 26, of course.

As can be seen from FIG. 1, the firing chamber is substantially larger than the dental restoration parts 18 illustrated, in practice at least twice as large as the latter.

According to the invention a detection device 28 is further provided which is configured as a thermal imaging camera in the exemplary embodiment illustrated. The axis of the detection device is directed at the dental restoration parts 18 through a window or possibly a through hole. For this purpose, it is mounted to the furnace in a fixed way by means of a support device 30, in the exemplary embodiment illustrated to the furnace base 12.

In the case of a firing furnace operated at negative pressure the firing hood is provided with a pressure-tight window through which the detection device 28 detects the dental restoration parts.

According to the invention it is favorable if the detection device 28 is arranged significantly above the furnace bottom 16 and tilted towards the furnace bottom, namely towards the center of the furnace bottom.

Even if not illustrated in FIG. 1, firing trays or other accommodation devices, or a central recess can be implemented in the furnace bottom which make clear to the user where to insert the dental restoration parts.

Due to the pivot position of the detection device 28 it also detects dental restoration parts which are positioned one behind the other as viewed from the perspective of the detection device, and this would not be the case if it was attached on the same plane as the furnace bottom 16.

In a modified embodiment, the firing hood is not provided with a window or through hole and the detection device 28 is active while the firing hood has not yet been closed with the furnace top 14. In this case, it has an unobstructed view of the dental restoration parts.

In the exemplary embodiment illustrated, the detection device 28 can be configured as an infrared sensor, as a thermal imaging camera or as an optical camera. In any case, it detects the two-dimensional size and basically also the shape of the dental restoration parts inserted.

In a modified embodiment the support device 30 can be pivoted at the furnace base 12 around a vertical axis, preferably the furnace axis, for instance by 90 degrees. In this embodiment the size and shape and number of the dental restoration parts inserted can also be detected three-dimensionally.

In this case, the output signal of the detection device 28 is supplied to the control device 24 which evaluates this output signal, for instance possibly by means of a recognition software.

The result of the detection is displayed numerically by the display device 29, in the present case in the form of a 2, as two dental restoration parts have been detected as crowns.

If a 6-unit bridge was present at this point instead of both dental restoration parts illustrated herein, the control device 24 would also evaluate the signal in this case.

The image detected would only correspond to one single dental restoration part with regard to the outline. It would, however, be considerably larger and be basically bent slightly in a sickle-shaped manner.

By means of a threshold recognition the control device 24 would determine in this case that the size of the dental restoration part recognized was smaller than a 7-unit and larger than a 5-unit bridge. Instead of showing the number 2 the display device 29 would thus display the number 6.

A numerical representation of this type is exceptionally easy to understand for the user of the furnace wherein it is to be understood that as a fixed marking the word "unit(s)" can be displayed below or next to the illustrated "2" on the display device 29.

In this connection, based on the present detection result with regard to the dental restoration parts, the dental furnace 10 suggests a firing program adjusted to the size of the dental restoration part standardized to that extent to the user via the control device 24 thereof. In the exemplary embodiment illustrated the user can change this firing program or make fine adjustments to it via the operating unit 26.

While misuse by an inexperienced dental technician is practically foreclosed due to the numerical default, an experienced dental technician can undertake a further readjustment and, for instance, adjust the closing time or the course of the firing curve.

According to the invention it is provided in any case that basic curves for a firing cycle are stored in the control device 24 which are defined with regard to the closing time on the one hand and with regard to the temperature curve on the other hand, but which can possibly be changed via the operating unit 26.

It is to be understood that in a way know per se the temperature in the firing chamber of the dental furnace 10 can be detected by a thermocouple or an infrared sensor and can be used as a control parameter for the desired temperature curve.

In a modified embodiment of the inventive dental furnace the unit specification of the dental restoration parts is displayed in a manner different than via Arabic numerals, for instance via any desired display symbols such as blocks or circles which each symbolize the units.

In a further advantageous embodiment a signal field is provided on the display device 28 which does not only symbolize the end of the firing cycle in a simple manner but, for instance, also the temperature in steps by change of color. For this purpose, the colors blue and red with a few intermediate shades are particularly favorable in order to display the temperature measured by the thermocouple of the dental furnace in a standardized way.

The display device 28 can also comprise a stop field which simplifies operation and indicates also to the inexperienced user that he must not remove the dental restoration part immediately after opening the furnace top 14, but only when cooling at the end of the firing cycle has made sufficient progress.

The invention claimed is:

1. A dental furnace for firing or pressing a dental restoration part which is receivable in the furnace, for pre-heating or after pre-heating in a pre-heating furnace, and which is positioned on a base, wherein the dental furnace comprises
    a firing chamber having a diameter larger than a largest dental restoration part to be fired,
    a control device,
    an operating unit for the dental furnace, and
    a detection device,
    wherein size and number of the dental restoration part(s) to be fired or to be pressed may be detected,
    wherein the detection device supplies the control device with a value or values of the detected size and the number of the dental restoration part(s) and wherein the control device is configured to quantify the value or values and offers the quantified value or values to the user in a number of units by means of the operating unit,
    wherein the control device is configured to suggest or adjust a firing program based on the number of units.

2. The dental furnace according to claim 1, wherein the size and/or the number and/or the weight of the dental restoration part(s) may be detected by the detection device of the dental furnace which is connected to the control device.

3. The dental furnace according to claim 1, wherein the dental furnace comprises a display device which can display the size and/or the weight of the dental restoration part(s) in units.

4. The dental furnace according to claim 3, wherein the operating unit comprises an operating panel which enables the setting of a press program or a firing program in units depending on the detected size or the detected weight of the dental restoration part(s).

5. The dental furnace according to claim 1, wherein the operating unit enables the control via voice control and/or gesture control and/or via a remote control.

6. The dental furnace according to claim 1, wherein a detection device detects the number and/or the size of the dental restoration part(s) to be fired or pressed and comprises an IR sensor or a camera.

7. The dental furnace according to claim 6, wherein the detection device supplies the control device with the output signal of the IR sensor or the camera and wherein the control device comprises an image recognition device which recognizes individual regions of the image detected and assigns them to the dental restoration parts.

8. The dental furnace according to claim 7, wherein the control device detects the number and/or size of the dental restoration parts by means of the image of the dental restoration parts detected by the IR sensor or the camera, based on a predetermined distance between IR sensor or camera and the dental restoration parts, and outputs the number and/or size based on the result of the recognition of the image of the dental restoration parts.

9. The dental furnace according to claim 8, wherein the camera is designed as a thermal imaging camera and wherein in the image recognition of the image of the dental restoration parts detected by the detection device an outline of hot areas corresponding to hot dental restoration parts differs from cold surroundings and wherein based on the image recognition the number and/or the size of the dental restoration parts is determined.

10. The dental furnace according to claim 9, wherein the detection device supplies the control device with a numerical value regarding the size and/or the weight of the dental restoration part and wherein the control device carries out a comparison with predetermined value ranges for quantification which is similar to rounding, and supplies the display device with a rounded result for display in units.

11. The dental furnace according to claim 10, wherein a detection device of the dental furnace is switched to active at the beginning of the press cycle or the firing cycle of the dental furnace and wherein when the dental restoration part(s) approaches and/or is inserted into and/or placed into/on the dental furnace, the detection device automatically detects the number, the size and/or the weight of the dental restoration part(s).

12. The dental furnace according to claim 11, wherein the dental restoration part(s) is intended for being received in the dental furnace on a firing tray and wherein a detection device of the dental furnace detects the firing tray with regard to the weight, the size and the density thereof and wherein the control device introduces the parameters of the firing tray into the quantification.

13. The dental furnace according to claim 12, wherein a firing aid of the dental furnace comprises an encoding via which a detection device of the dental furnace recognizes it and carries out an automatic adjustment of the firing program or the press program.

14. The dental furnace according to claim 13, wherein the control device carries out a correction factor for controlling the firing program or press program upon recognition of a firing tray or other firing aid by the detection device and offers the correction as a correction factor or as a correction value to the user for selection on a display device (29).

15. The dental furnace according to claim 1, wherein the dental furnace is a firing furnace or a press furnace.

16. The dental furnace according to claim 1, wherein the dental restoration part is positioned centrally on the base.

17. The dental furnace according to claim 1, wherein the diameter of the firing chamber is at least twice as large as the largest dental restoration part to be fired.

18. The dental furnace according to claim 12, wherein the size of the firing tray comprises height and/or diameter and the density of the firing tray comprises mass.

19. The dental furnace according to claim 13, wherein the firing aid comprises a firing tray, comprises an encoding via which a detection device of the dental furnace (10) recognizes it and carries out an automatic adjustment of the firing program or the press program.

\* \* \* \* \*